(12) United States Patent
Russi

(10) Patent No.: US 12,303,175 B2
(45) Date of Patent: May 20, 2025

(54) EXTRAMEDULLARY INTERNAL BONE LENGTHENING AND FIXATION DEVICE WITH DYNAMIC AXIAL STABILIZATION

(71) Applicant: Martin Russi, Montevideo (UY)

(72) Inventor: Martin Russi, Montevideo (UY)

( * ) Notice: Subject to any disclaimer, the term of this patent is extended or adjusted under 35 U.S.C. 154(b) by 446 days.

(21) Appl. No.: 17/549,474

(22) Filed: Dec. 13, 2021

(65) Prior Publication Data
US 2022/0183729 A1 Jun. 16, 2022

Related U.S. Application Data

(60) Provisional application No. 63/124,347, filed on Dec. 11, 2020.

(51) Int. Cl.
| | |
|---|---|
| *A61B 17/80* | (2006.01) |
| *A61B 17/68* | (2006.01) |
| *A61B 17/82* | (2006.01) |
| *A61B 17/84* | (2006.01) |
| *A61B 17/00* | (2006.01) |

(52) U.S. Cl.
CPC ........ *A61B 17/8004* (2013.01); *A61B 17/683* (2013.01); *A61B 17/8023* (2013.01); *A61B 17/82* (2013.01); *A61B 17/848* (2013.01); *A61B 2017/00991* (2013.01); *A61B 2017/681* (2013.01)

(58) Field of Classification Search
CPC ... A61B 17/60; A61B 17/66; A61B 2017/681; A61B 17/8004; A61B 17/8023; A61B 17/8076; A61B 17/82; A61B 17/842
See application file for complete search history.

(56) References Cited

U.S. PATENT DOCUMENTS

| | | | | |
|---|---|---|---|---|
| 6,106,525 A | * | 8/2000 | Sachse | F15B 15/1414 606/59 |
| 7,635,365 B2 | * | 12/2009 | Ellis | A61B 17/8076 606/71 |
| 8,267,974 B2 | * | 9/2012 | Schlafli | A61B 17/8047 606/291 |
| 11,612,415 B2 | * | 3/2023 | Liu | A61B 17/8605 606/57 |
| 2005/0234448 A1 | * | 10/2005 | McCarthy | A61B 17/8004 606/57 |
| 2006/0276896 A1 | * | 12/2006 | Fallin | A61B 17/82 623/908 |

(Continued)

FOREIGN PATENT DOCUMENTS

WO WO-2020069627 A1 * 4/2020 ......... A61B 17/7016

*Primary Examiner* — Larry E Waggle, Jr.
(74) *Attorney, Agent, or Firm* — Muncy, Geissler, Olds & Lowe, P.C.

(57) ABSTRACT

An internal extramedullary bone lengthening device with dynamic axial stabilization includes two plate-like bone fixation elements shaped as a locked plate with bone fixation in a proximal sector and a distal sectors, wherein the bone fixation elements comprises a double-locking canulated assembly configured to allow bone fixation with tension Kirschner wires and/or tension cerclage wires; an intermediate sliding zone with a tubular or semi-tubular shape, the intermediate sliding zone configured to support the Kirschner wires and/or the tension cerclage wires; and a motor configured to actuate the intermediate sliding zone.

1 Claim, 22 Drawing Sheets

(56) References Cited

U.S. PATENT DOCUMENTS

| | | | |
|---|---|---|---|
| 2007/0173837 A1* | 7/2007 | Chan | A61B 17/66 606/63 |
| 2009/0093890 A1* | 4/2009 | Gelbart | A61B 17/7062 623/24 |
| 2021/0186643 A1* | 6/2021 | Chevalier | A61B 17/86 |
| 2022/0015751 A1* | 1/2022 | Chevalier | A61B 17/8009 |

* cited by examiner

EXTRAMEDULLARY INTERNAL BONE LENGTHENING AND FIXATION DEVICE WITH DYNAMIC AXIAL STABILIZATION

FIELD OF THE INVENTION

The present invention refers to the devices, provisions or means used in surgery, more preferably for bone lengthening, transport or angular correction, more particularly the invention refers to an extra-medullar locked internal bone lengthening and fixation device that allows for it to be fixed to the bone by locked screws, but also by tension-locked Kirschner wires or tension-locked wires. It presents an intermediate zone between the two sliding bone fastening systems that can be driven by the current internal, magnetic, electromagnetic or electric bone lengthening systems used for intramedullary motorized lengthening nails.

By providing this locked plate-like device the ability of attaching to the bone with tension Kirschner wires, this would allow to generate a non-absolute relative stability of the locked plate systems, which would allow the development of a locked extramedullary bone lengthening system with dynamic axial stability. The ability to determine axial dynamic stability equates them to Ilizarov's hybrid or transfixing circular unilateral external bone lengthening systems but developed internally.

Even if reference is made in the present disclosure to an internal, extramedullary bone stabilization and lengthening set, with fixation and double cannulated block of Kirschner rod for trauma surgeries, it is clear that the invention can be considered and used without any inconvenience in any type of surgery in which a part of the body must be fixed and lengthened.

DESCRIPTION OF PRIOR ART

Bone lengthening, or surgical lengthening, is a surgical process used to correct congenital bone malformations and lengthening bones of the body or treating segmental bone defects (internal bone lengthening). A corticotomy or osteotomy is used to generate a bone continuity solution, slowly separating the ends of the bone after a period of relative latency, allowing for the generation of a new bone in that space (distraction osteogenesis). When the desired or possible length is reached, a consolidation phase is carried out in which the bone is allowed to continue healing. The process has the benefit of simultaneously increasing the length of bone and the volume of surrounding tissues.

To carry out this task of surgery, a bone stabilization device is required which can be external (circular or unilateral, transfixing or not) or internal intramedullary such as magnetic or electrical lengthening nails that currently exist.

We propose an internal extramedullary locked plate-like lengthening and stabilizing device with the possibility of fixing it to bone with locked screws and Kirschner locked wires or nails, wherein locked cerclage cables or wires can also be used, said device having a motorized sliding space in the middle of the plate, wherein any of the current systems used in intramedullary lengthening nails can be used.

At present, extramedullary bone fixation systems (osteosynthesis plate) for trauma surgery can use locked and even variable angle screws by determining a screw-to-plate bond to achieve a more stable and rigid plate-bone fixation, acting as an internal fastener, thereby avoiding the application of the plate to the bone and therefore the necrosis of the periosteum and bone in this sector, unlike the bone compression produced by unlocked plates.

The locked fixation of the screw to the plate makes it a more stable system for fixing bone continuity solutions in osteopenic bones.

Another bone fixation device, but an external one, is the circular assembly of Ilizarov, which is a transfixing circular device for bone stabilization, compression and distraction. For bone fixation tension Kirschner wires are used. Tension kirschner wires or Schanz nails that can also be used in this system, which go through soft parts such as skin, cells, muscle, while sparing large vessels and nerves, can produce intolerance, development of infectious processes, or intense pain.

Other external bone lengthening stabilization devices are Orthofix-like unilateral systems or tube AO systems; these systems use Schanz nails with the same drawbacks already described above.

Both locked osteosynthesis plates and external lengthening fixation elements have been shown to function correctly in practice. However, we will focus on the main presented disadvantages in order to explain the development of the idea that is to be protected.

The disadvantage of the locked plate is that it determines a very rigid system of bone fixation, generating absolute stability of the bone continuity solution, this determines that an anatomical reduction of the fracture focus is needed for its consolidation.

The disadvantage of external stabilization systems is their intolerance due to pain, infection in the path of the Schanz nails or Kirschner wires, or injury to soft parts during the lengthening process.

Motorized bone stabilization-lengthening nails have been a solution to these problems, however they present difficulties that should be solved, such as:

They need a wide and long medullary canal size for placement.

They pass through the physis in the growing skeleton.

Anterograde femur placement may result in avascular necrosis of the femoral head in the growing skeleton when starting from the trochanteric fossa.

Their placement starting from the trochanter tip may lead to proximal femur *varus*

They have to go through joins for their placement (retrograde femur-anterograde tibia)

They need milling of the medullary canal.

They lengthen in the anatomical axis of the bone, being an inconvenience in the femur which can lead to an important *varus* in considerable lengthening.

They can be difficult to remove, especially if the device breaks inside the canal.

The internal extramedullary stabilization-lengthening devices that we want to protect allow to solve the disadvantages presented previously, determining locked plate-like lengthening systems. All lengthening systems currently used in intramedullary lengthening can be used. We have developed bone fixation elements such as locked Kirschner wires or locked cerclage wires, which would also mitigate the absolute stability of locked plates, allowing a dynamic locked stabilization system of internal extramedullary lengthening.

BRIEF DESCRIPTION OF THE INVENTION

It is therefore an object of the present invention to provide a new internal locked extramedullary bone stabilization-lengthening plate-like device with dynamic axial stabilization for trauma surgeries, which provides greater ease of placement, practicality for performing bone lengthening, avoiding previously described disadvantages of the other external lengthening stabilization systems, as well as the disadvantages of internal intramedullary systems.

It is also the object of the present invention, to provide a new internal extramedullary locked bone stabilization-lengthening device (as shown in FIGS. 1 and 2), with dynamic axial stabilization, which has a canulated double-locking assembly for bone fixation elements such as Kirschner wires or cerclage wire. (As shown in FIGS. 3 and 4.)

It is also the object of the present invention to provide an internal extramedullary locked bone stabilization-lengthening device with dynamic axial stabilization which has a canulated double-locking assembly that allows the placement of transfixing tension Kirschner wires, which are the fundamental principle for the development of bone fixation systems with the Ilizarov concept (pressure Kirschner as shown in FIG. 6B).

It is also the object of the present invention to provide an internal extramedullary locked bone stabilization-lengthening device with dynamic stabilization, which has a canulated double-locking assembly that allows a mixed fixation system to bone, that is, extramedullary internal lengthening system with extramedullary and intramedullary stabilization (as shown in FIG. 7).

It is also the object of the present invention to provide an internal extramedullary locked bone stabilization-lengthening device with dynamic stability of circumferential development to the bone which has canulated double-locking that allows the placement of tension Kirschner wires, transfixing elements (internal Ilizarov) and locking system of locked screws making hybrid fixing mechanisms. (As shown in FIGS. 6A, 6B and 6C)

It is also the object of the present invention to provide an internal extramedullary locked bone stabilization-lengthening device with dynamic stability, for development with a double plate. This double plate can be fixed with tension Kirschner wires and/or tension cerclage wires, and also locked screws and even variable angle locked screws can also be counted as bone anchoring elements. (As shown in FIGS. 8A, 8B and 8C).

BRIEF DESCRIPTION OF THE DRAWINGS

For greater clarity and understanding of the object of this invention, it has been illustrated in several figures, in which it has been represented in one of the preferred embodiments, all by way of example, wherein.

DETAILED DESCRIPTION OF THE INVENTION

Referring to FIGS. 1, 2, 5, 6, 7 and 8, they show that the invention consists of a new internal extramedullary bone stabilization-lengthening system with dynamic axial stability. This system allows the development of lengthening systems in bones which nowadays, because of their size or shape, do not allow intramedullary internal lengthening systems, being able to determine a relative stability of the locked system, thanks to bone stabilization with tension-locked Kirschner wires and/or locked cerclage cables or wires protected by a previous patent (U.S. patent application Ser. No. 17/006,098. Priority date. 30/8/2019. Not published). As seen in FIGS. 3 and 4 and Photos 1, 2, 3 and 4.

Figure 1:
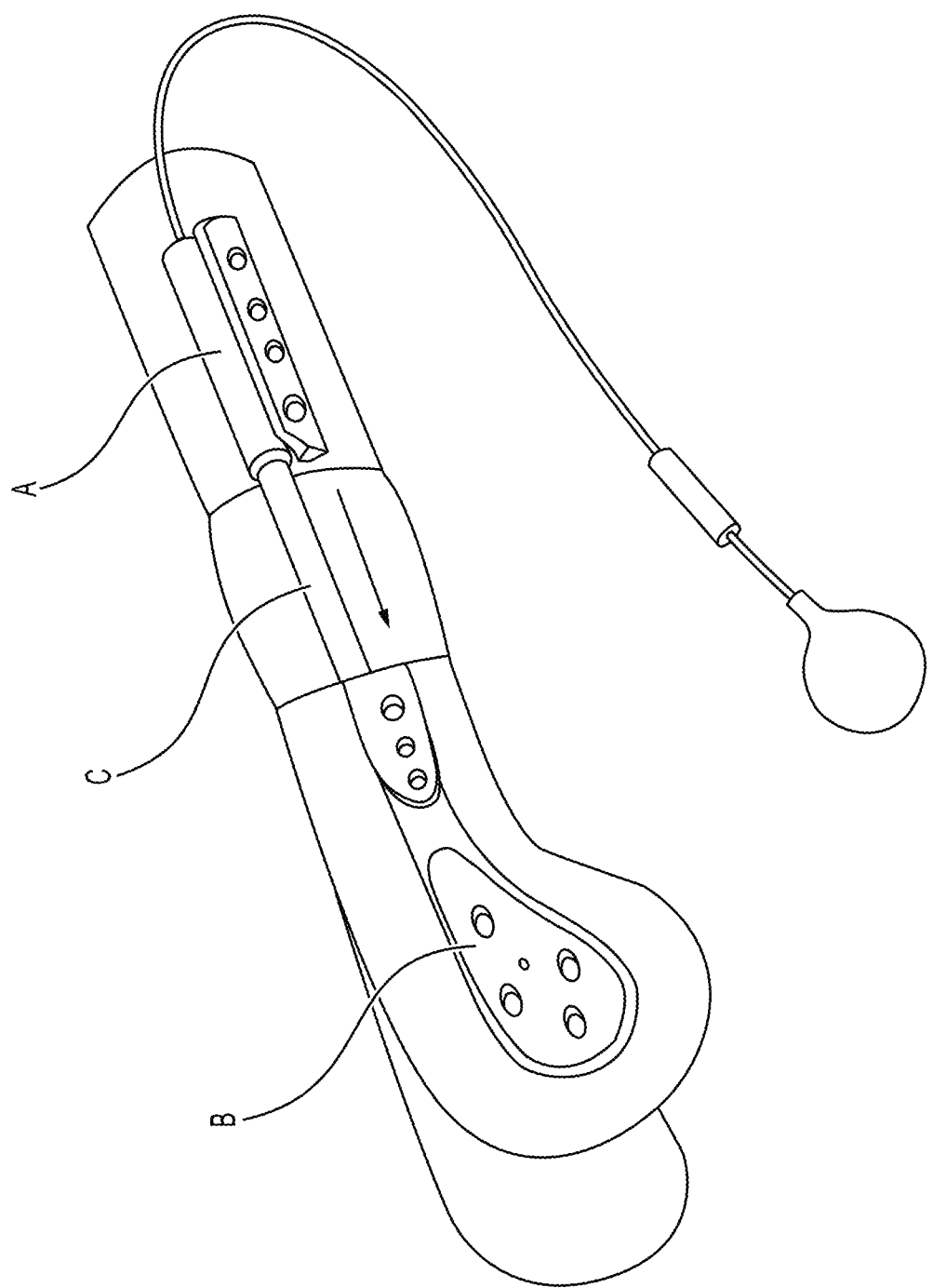
FIGS. 1 and 2 are perspective views of a locked plate-like embodiment for both femur and tibia, which, in the lengthening segment, can use any of the lengthening forms currently developed for intramedullary nails.
Figure 2:
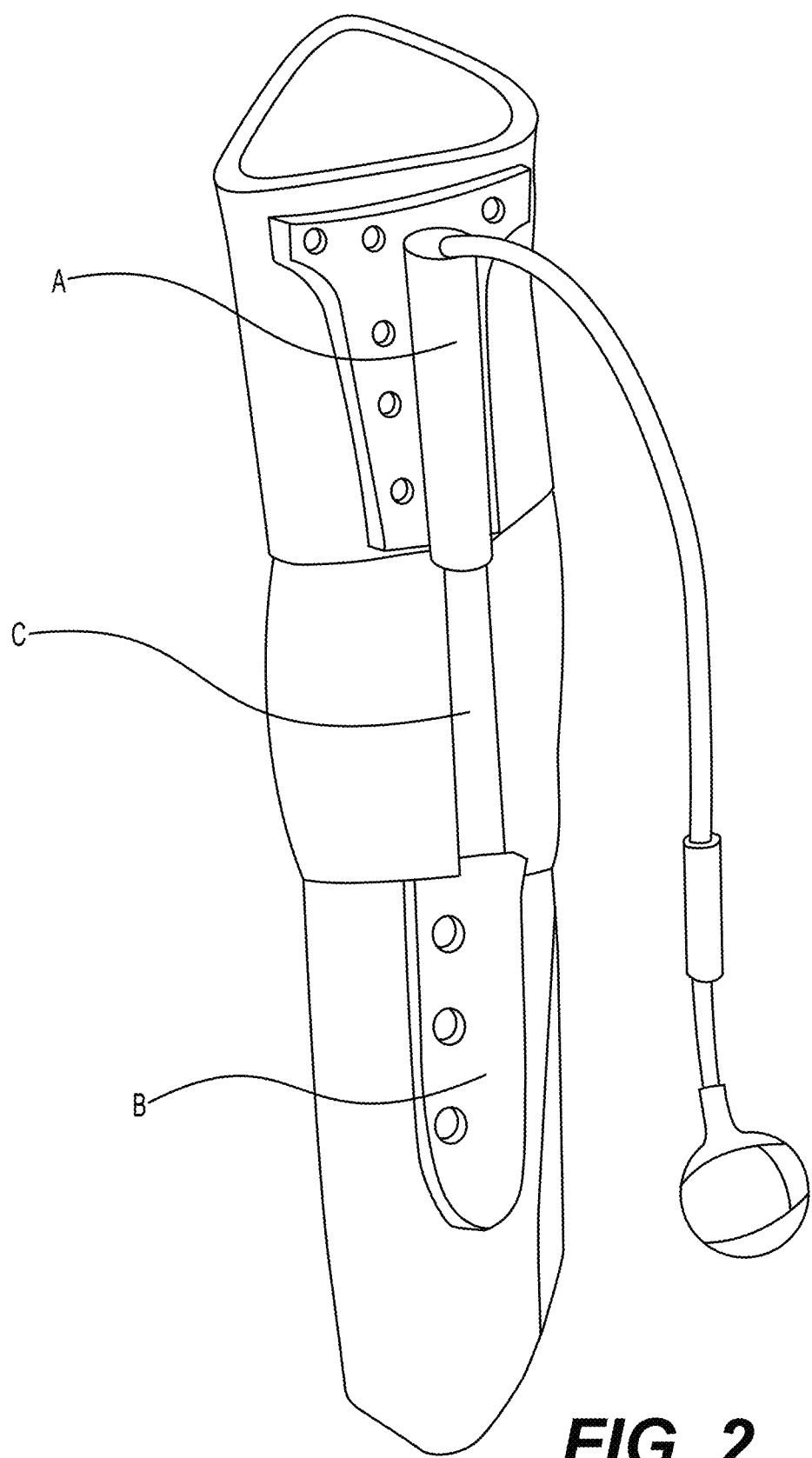
Figure 3:
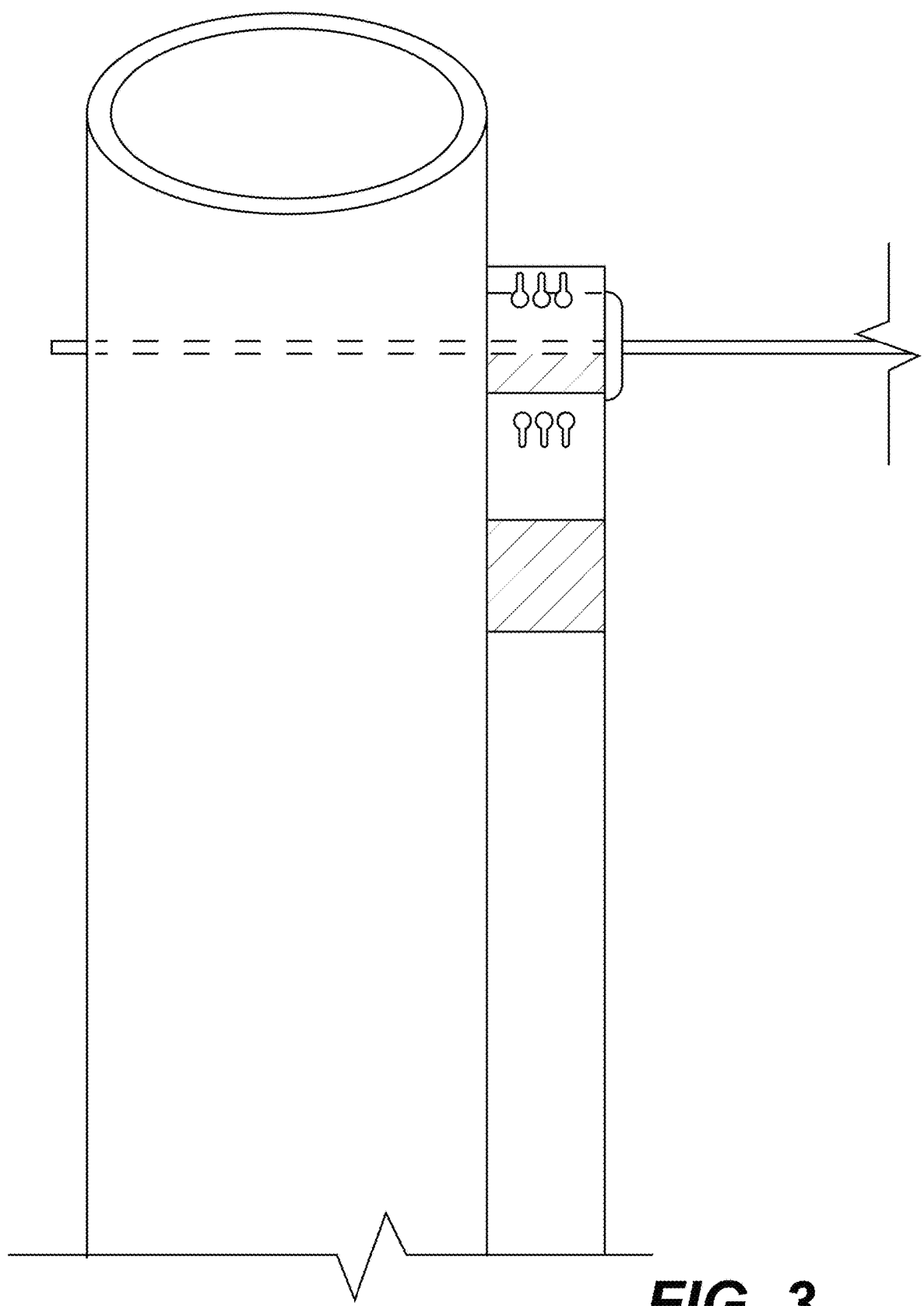
FIGS. 3 and 4 show a perspective view of a portion of the canulated double-locking and fixation assembly for plate-to-bone stabilization with locked Kirschner wires (system protected under patent, U.S. patent application Ser. No. 17/006,098. Priority date. 30/8/2019. Not published).
Figure 4:
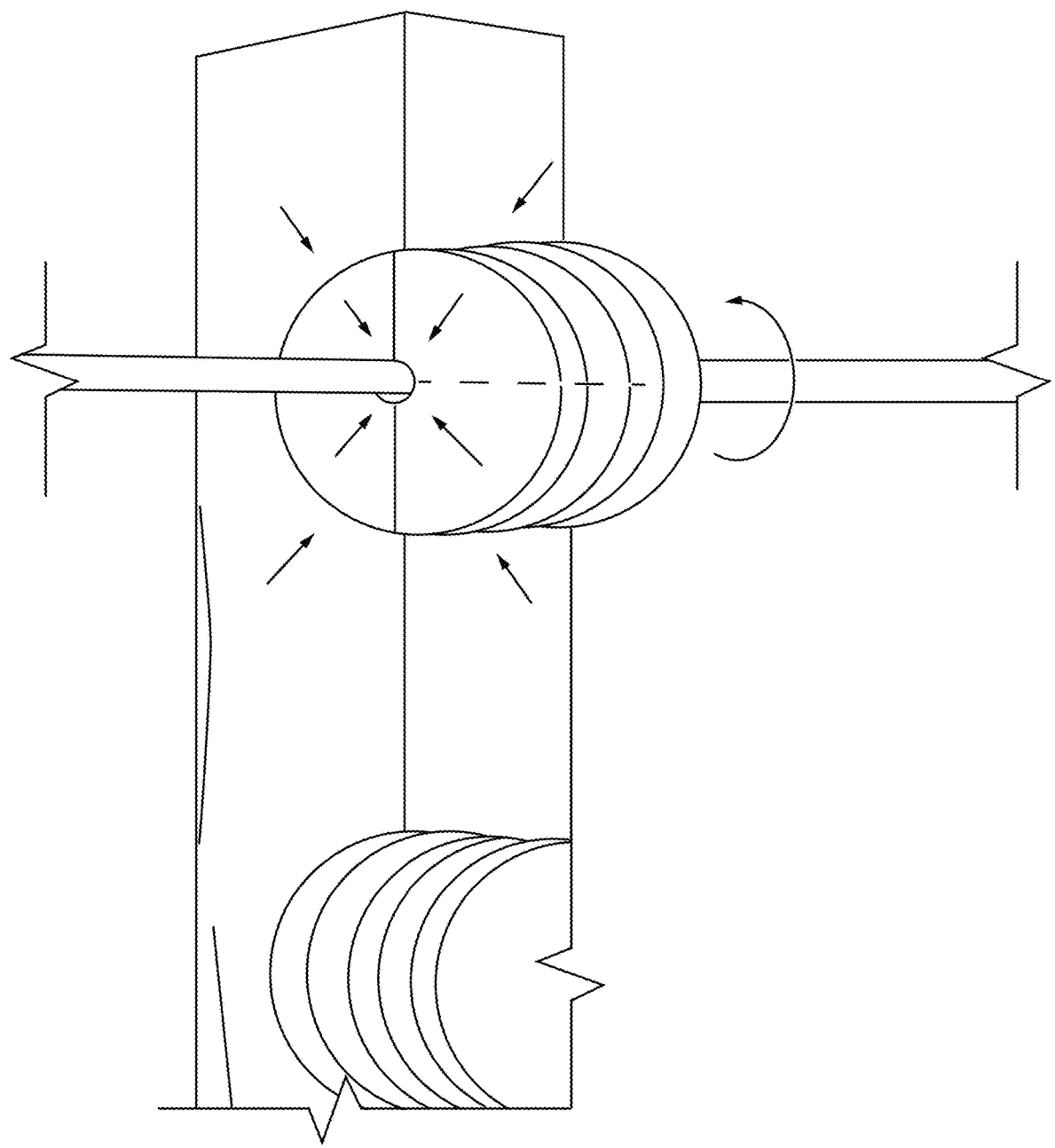

According to FIGS. 1 and 2, the invention as a whole consists of at least two locked plate-like bone fixation elements, which allow double-locking canulated systems for the attachment of tension Kirschner wires to the bone, as shown in FIGS. 3 and 4 and photos 1, 2, 3 and 4. These two bone fixation elements (a and b) are attached in the intermediate zone by a (telescopic c) tubular or semi-tubular sliding system that can be motorized by currently used systems in intramedullary (magnetic, electro or electromagnetic) nails allowing bone lengthening.

Figure 5A:
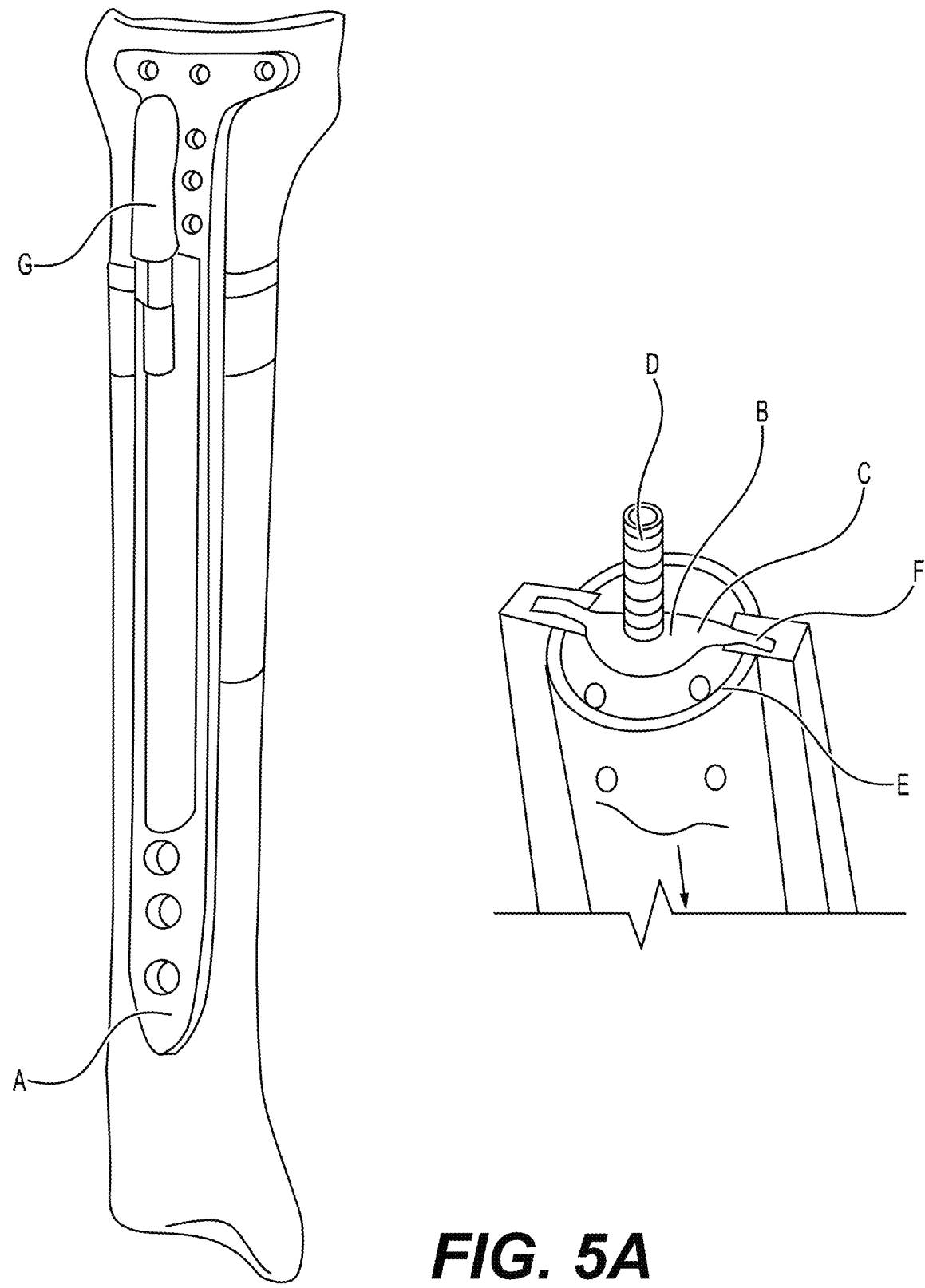
FIG. 5A shows a perspective view of a locked plate for extramedullary stabilization-lengthening that allows bone transport of a bullet fragment, similar to Orthofix type extramedullary systems but internal, wherein the magnetic or electric motor allows the rotation of a threaded rod and this allows to lower the intermediate fixation system for bone transport, this system could be developed to allow rotation in both directions generating bone distraction or compression.

According to FIG. 5A, the development of a locked plate (a) is shown, with bone fixation elements in its proximal and distal portions for both locked screws that can be of variable angle as well as supporting the double-locking canulated assembly to lock tension Kirschner wires or cerclage wires (mixed bone fixation systems as shown in photos 5A and 5B), featuring a central sliding space in the middle of the plate where there is a bone fixation area that supports locked Kirschner wires (b) and cerclage wires having a central threaded bore (c) which slides on a threaded rod (d), which acts in a closed chamber (e). This sliding element with bone attachment zones has two side wings (f) that slide inside the plate to prevent it from rotating while sliding down the threaded rod.

At one end, the threaded rod has a motorized rotation system (g) that can be electric, magnetic or electromagnetic as current motorized systems of intramedullary nails.

Figure 5B:
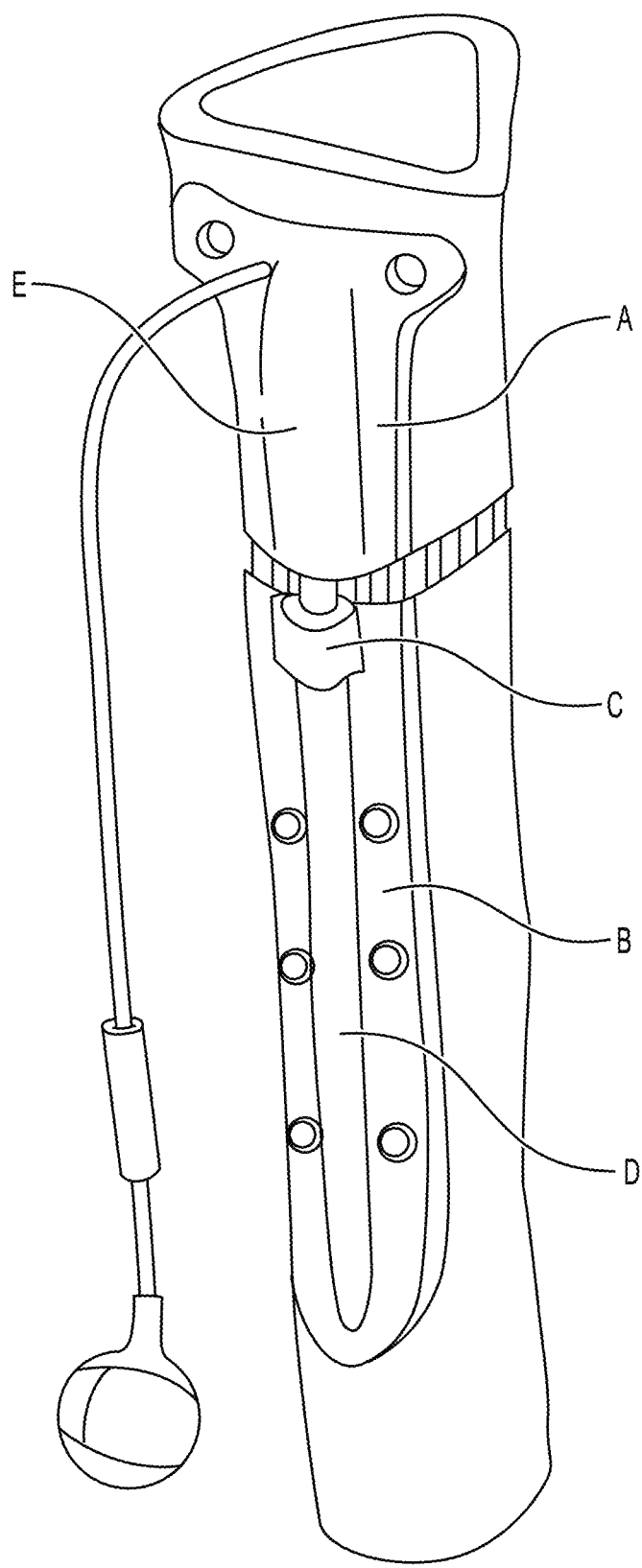
FIG. 5B shows a perspective view of a locked plate for extramedullary stabilization-lengthening that allows bone lengthening, similar to Ortofix type extramedullary systems but internal, wherein the magnetic or electric motor allows the rotation of a threaded rod and this allows to lower the distal fixation system for bone lengthening, this system could be developed to allow rotation in both directions generating bone distraction or compression.

According to FIG. 5B, a perspective view of an internal extramedullary bone lengthening device with dynamic axial stabilization comprising at least two bone fixation elements is shown. The bone fixation elements are two locked plate-like systems with bone fixation in the proximal (a) and distal (b) sectors, which allows the use a double-locking canulated assembly as a form of bone fixation which, in turn, allows for bone fixation by tension Kirschner wires and/or tension cerclage wires. This locked plate, consisting of two proximal and distal elements, is joined in the intermediate zone by a central sliding zone (c), advancing into a chamber guided by a threaded central rod (d) passing through it and rotating by motorized means one of the two bone fixation elements, the motor is located on the other plate element (e), which can be at the proximal or distal end thereof actuating by systems that can be electric, magnetic or electromagnetic, such as those used in intramedullary internal lengthening with motorized nails.

Figure 6A:
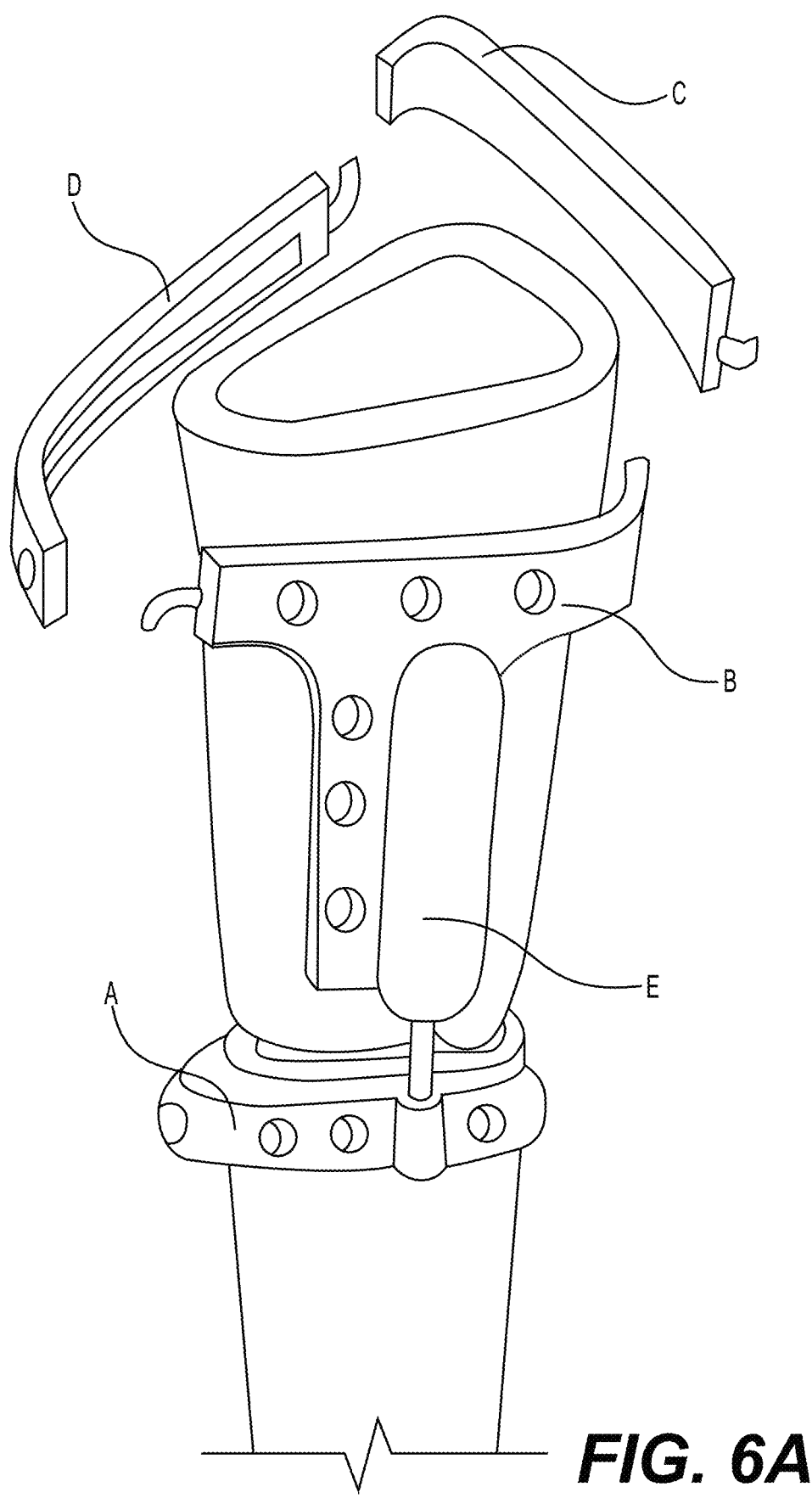
FIGS. 6A, 6B and 6C show a perspective view of an internal extramedullary lengthening stabilization system circular to the bone with tension Kirschner wires (internal Ilizarov).
Figure 6B:
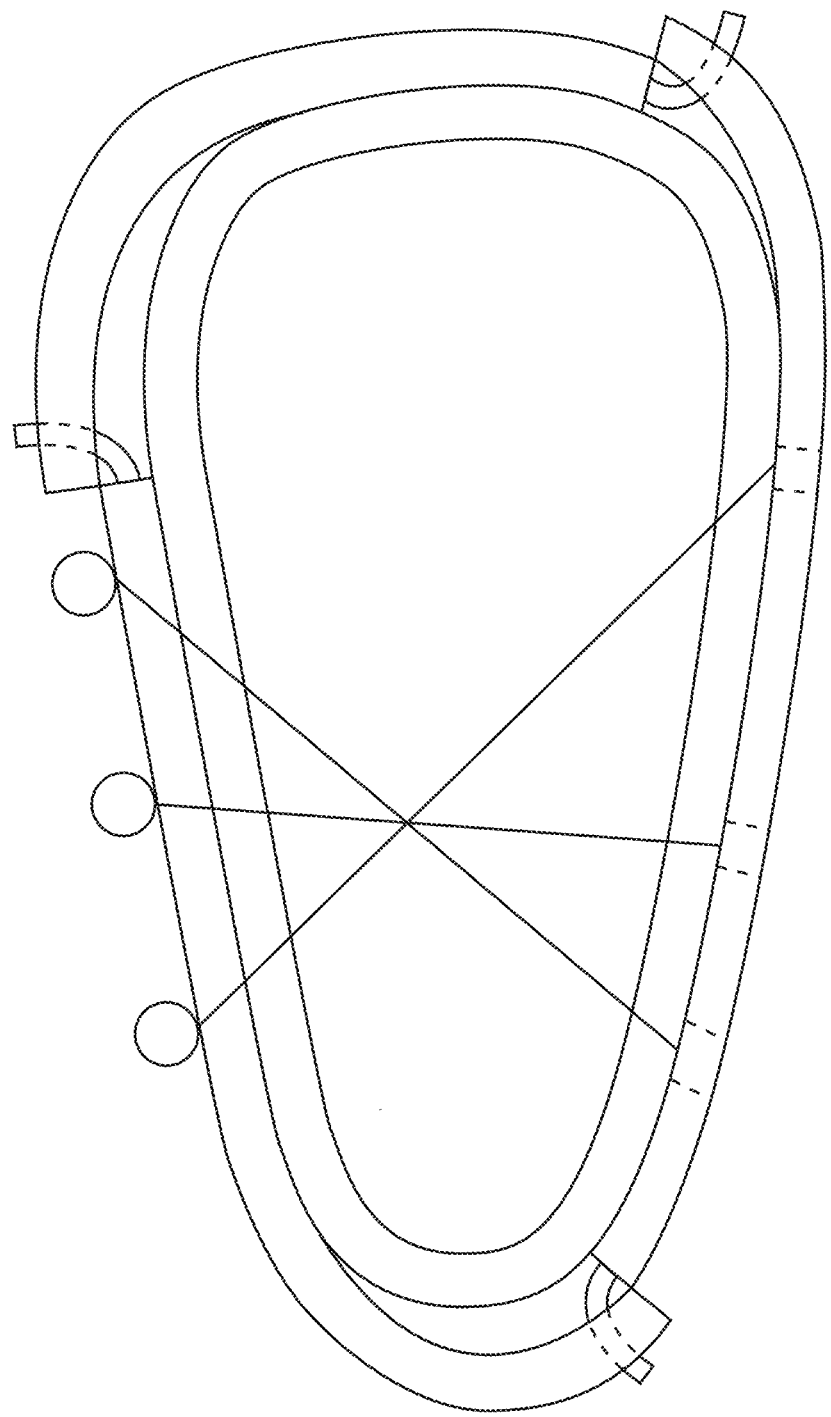
Figure 6C:
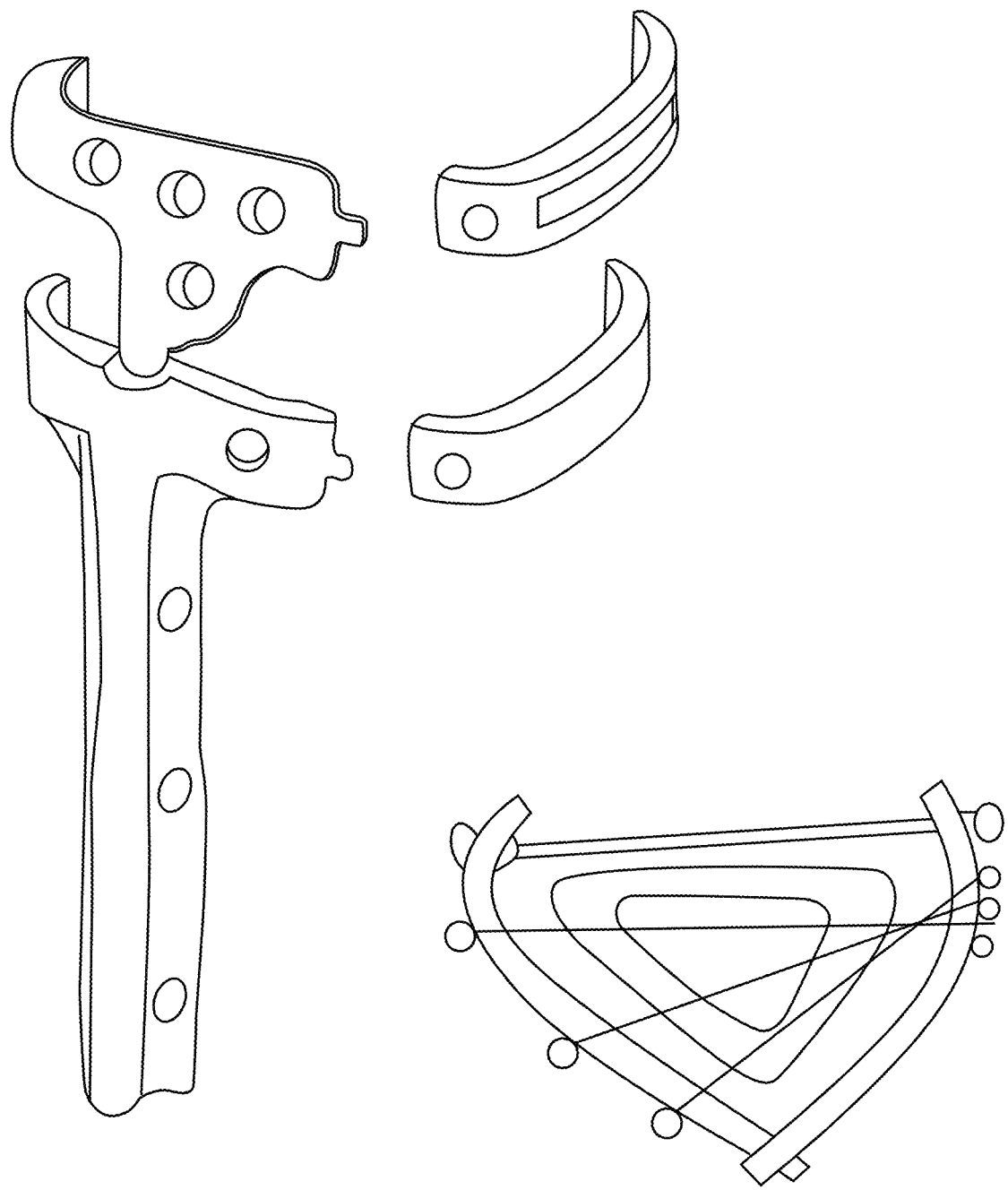

According to FIGS. 6A and 6B, the development of a stabilization system consisting of at least two closed circular periosseous elements (a) to maintain the tensile stress of Kirschner wires is shown.

These closed ring-like elements can be generated by joining three elements (b, c and d) as shown in the figure for proximal tibia, at one of these three elements is attached the sliding system (e), which is continued with the distal fixation element.

These closed ring-shaped elements allow the use of locked screws which can be of a variable angle and also allow the use of the double-locking assembly for tension Kirschner wires, these bone fixation systems are attached by a sliding system similar to those developed for intramedullary lengthening but arranged in an extramedullary form, as shown in the figure, allowing internal bone lengthening, with locked extramedullary systems of dynamic axial stabilization.

Figure 7:
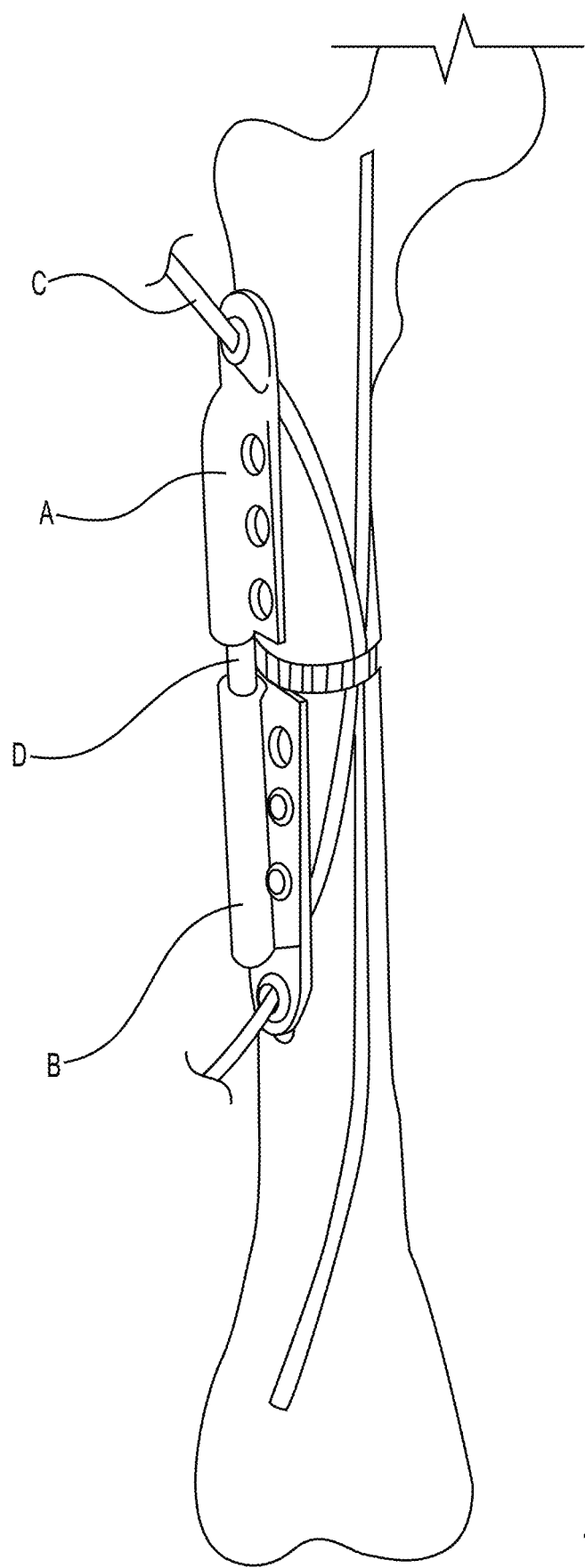
FIG. 7 shows a perspective view of an extramedullary internal lengthening stabilization system, wherein the stabilization system is a mixed extra and intramedullary system.

According to FIG. 7, a perspective view of an extramedullary internal fixation and lengthening system consisting of 2 locked plate-like bone fixation elements (a and b) is shown, which allow the use of a double-locking canulated element for attaching intramedullary elements such as TENS or Ender nails (c) and bone fixation elements, such as tension Kirschner wires, tension cerclage wires and locked screws that may or may not be of a variable angle.

These two locked plate-like elements are joined in their central portion by a tubular or semi-tubular (telescoped) sliding zone motorized by current systems used for current intramedullary nails.

Figure 8A:
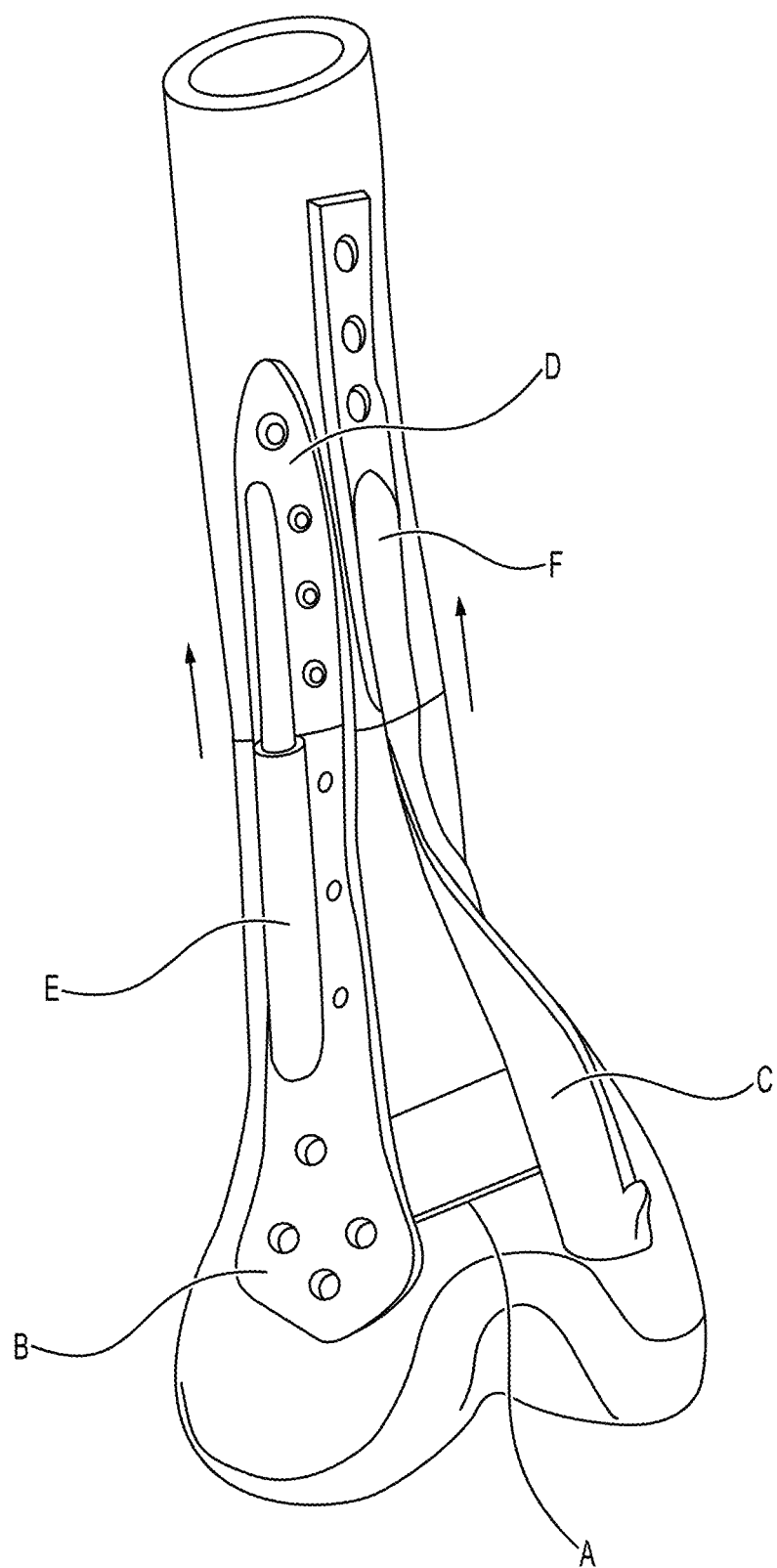
FIGS. 8A, 8B and 8C show a perspective view of an internal extramedullary lengthening stabilization system, wherein the bone stabilization system is a double plate with interconnection therebetween by tension Kirschner wires and/or cerclage wires.

According to FIG. 8A, a perspective view of an internal locked extramedullary lengthening system which allows the use of tension Kirschner wires and/or cerclage wires joining both plates (a) is shown.

This specific development model for distal femur shows an external slide plate (b) with proximal and distal anchoring and a slide system similar to those already analyzed, and an internal plate (c) of helical arrangement wherein its proximal and distal portions also present attachment elements to locked bone, which allows the use of tension Kirschner wires, locked screws that can be of a variable angle and tension cerclage wires. Both plates can be joined in the distal portion using tension Kirschner wires (a), thereby closing a lengthening circuit. The two plates locked by tension-locked cerclage can be joined in the proximal portion, as shown in figure (d).

The sliding motor goes on the lateral straight plate (e), the helical plate presenting a sliding system that accompanies the lengthening guided by the lateral plate (f)

Figure 8B:
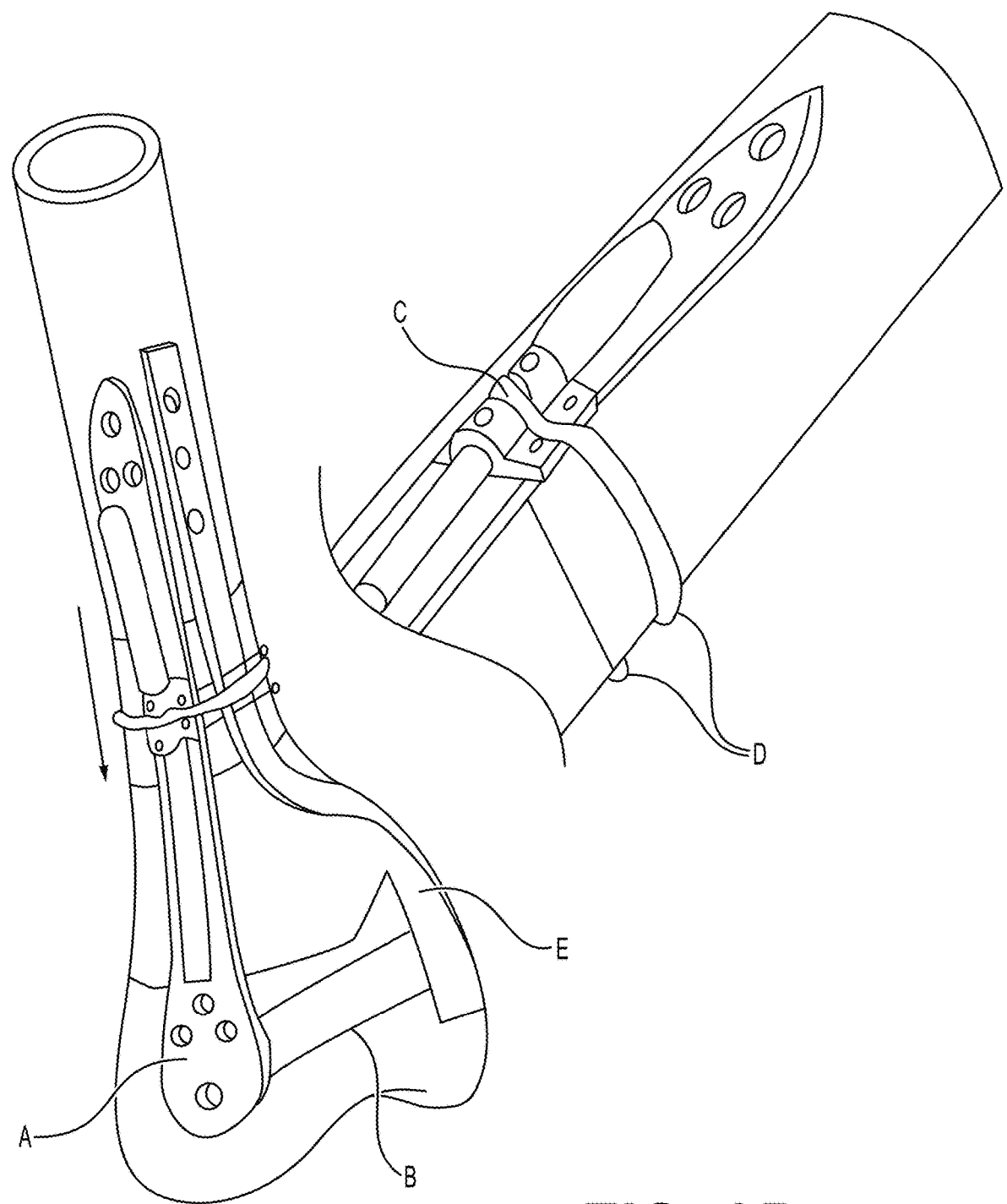

According to FIG. 8B, a perspective view of an internal locked extramedullary lengthening system for anterograde bone transport is shown, wherein the lateral locked plate (a) is a continuous plate that allows the use of both proximal and distal locked bone anchoring elements for both locked Kirschner wires (b) and locked screws that can be of a variable angle, which features a sliding element (c) in its central sector that also features bone anchoring elements for the bullet fragment (d). This central element is slid by actuating the motor located in the proximal sector of the locked plate as shown in the figure. In this case of bone transport, the helical locked plate can be continuous (e), without having a central sliding element, featuring proximal and distal locking holes that allow the use of both locked screws that can be of variable angle and locked Kirschner wires that allow attachment with the side plate by tension.

Figure 8C:
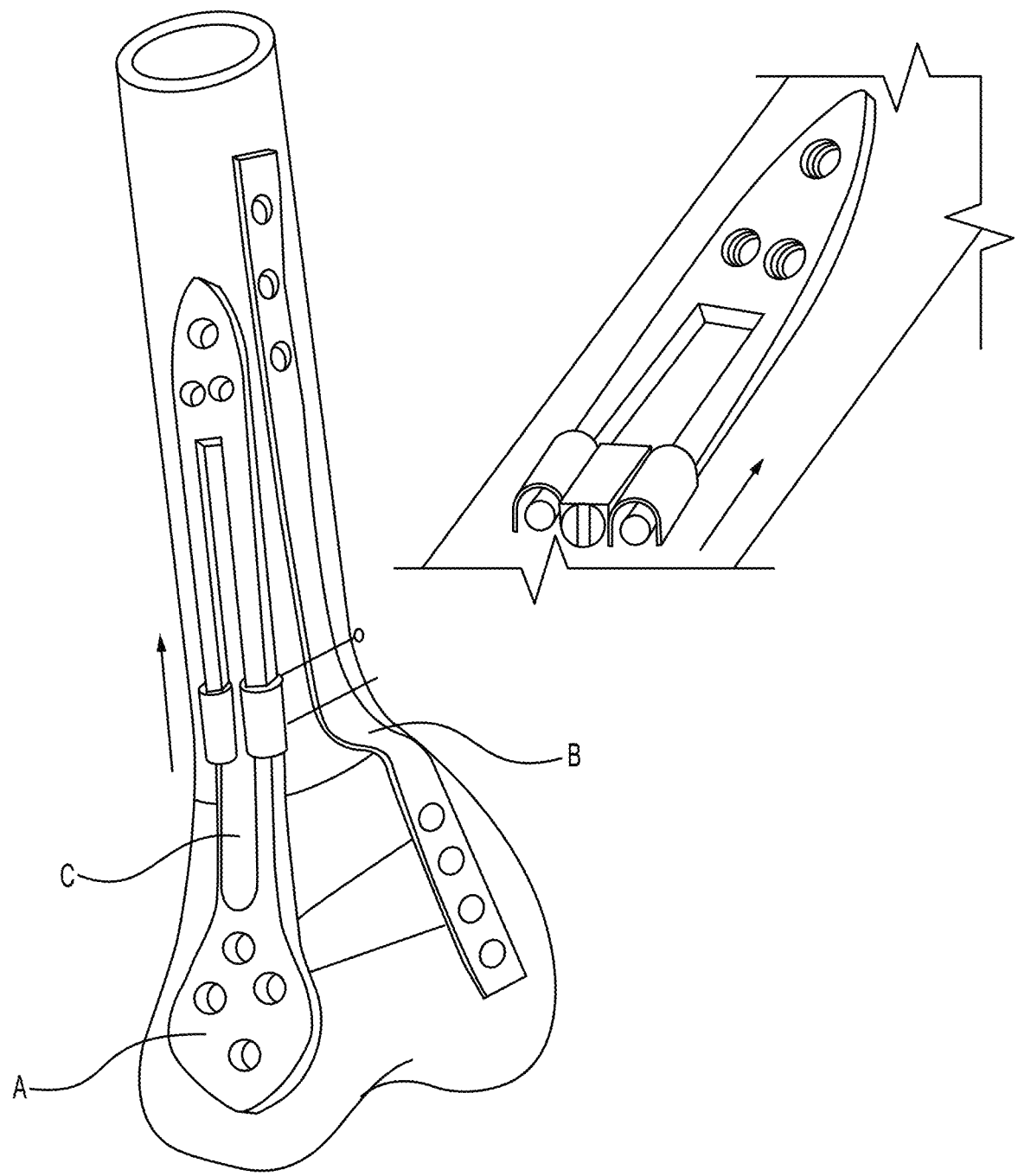
Figure 9A:
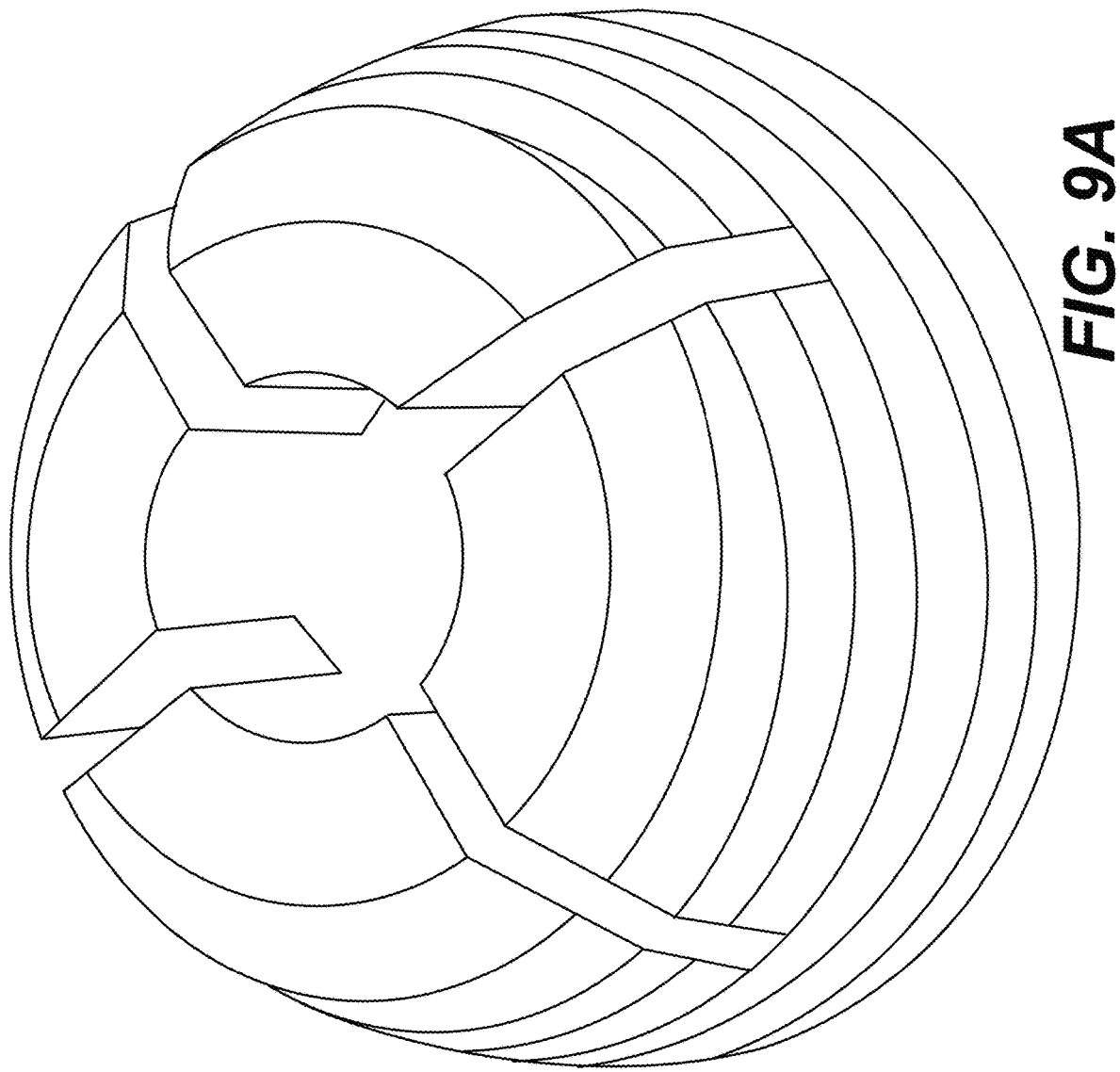
FIGS. 9A and 9B show a perspective view of the double block head with its central cannulated system and the slits that close when threading and of the double block head attached to the cannulated screwdriver.
Figure 9B:
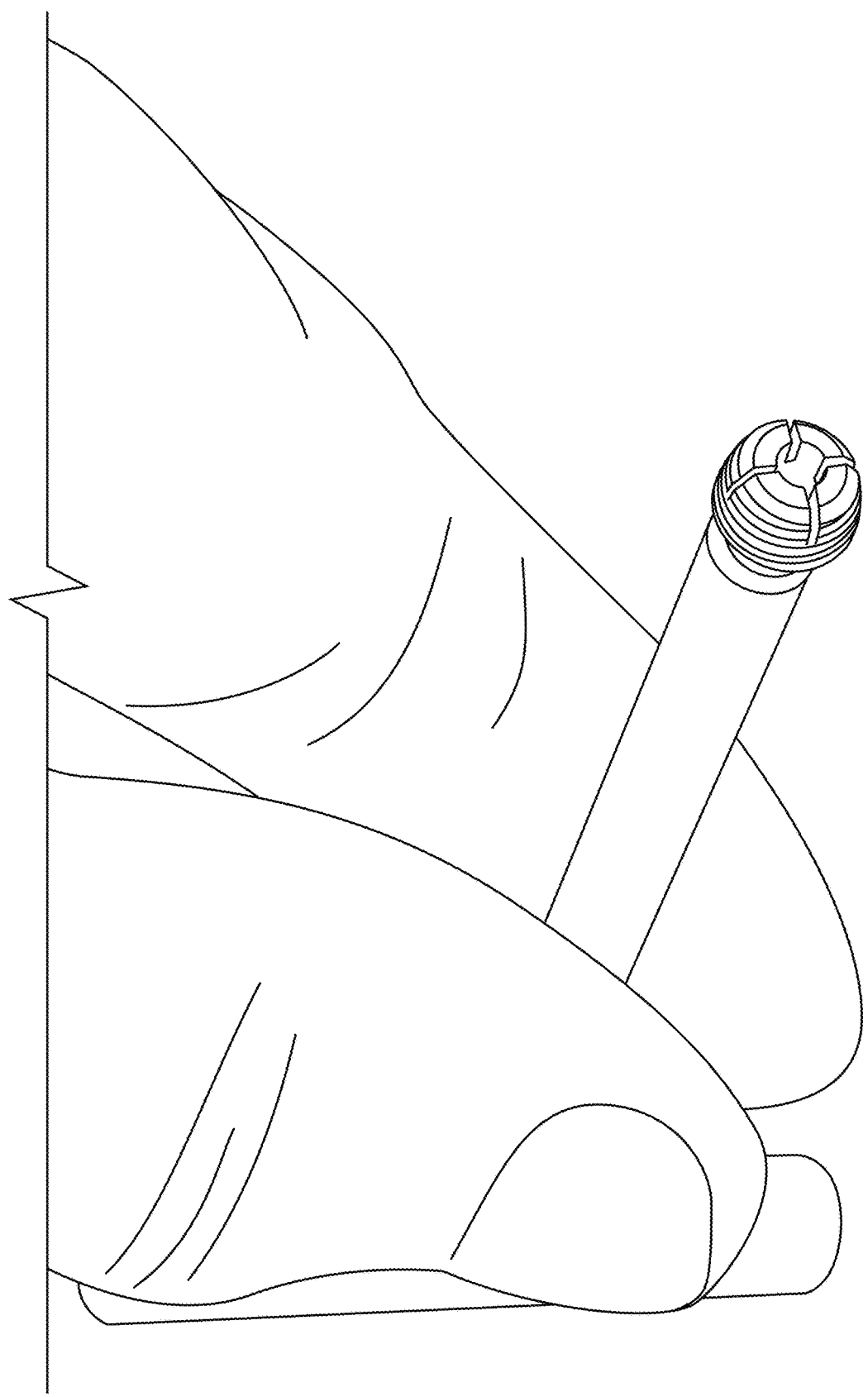
Figure 10:
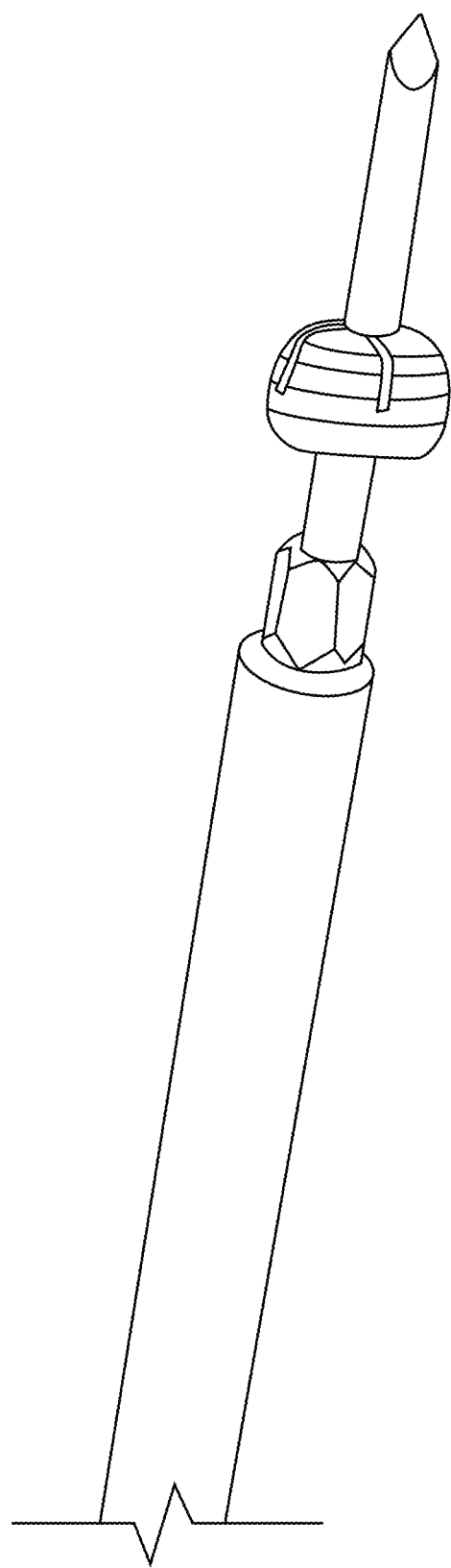
FIG. 10 show a perspective view of a double block head with Kirschner going through its cannulated system and cannulated screwdriver
Figure 11A:
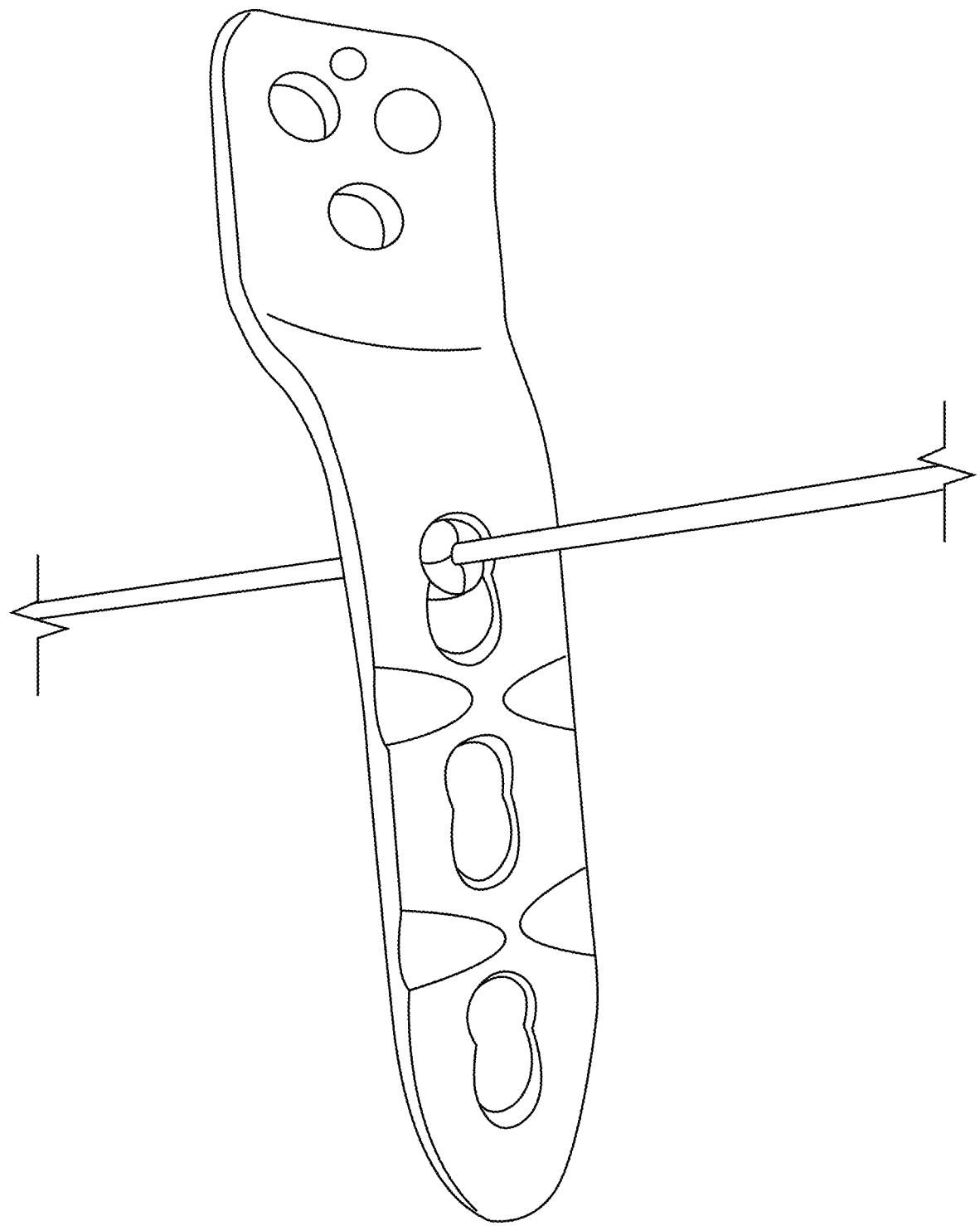
FIGS. 11A and 11B show a perspective view of a Kirschner Nail locked to plate by a double locking cannulated head.
Figure 11B:
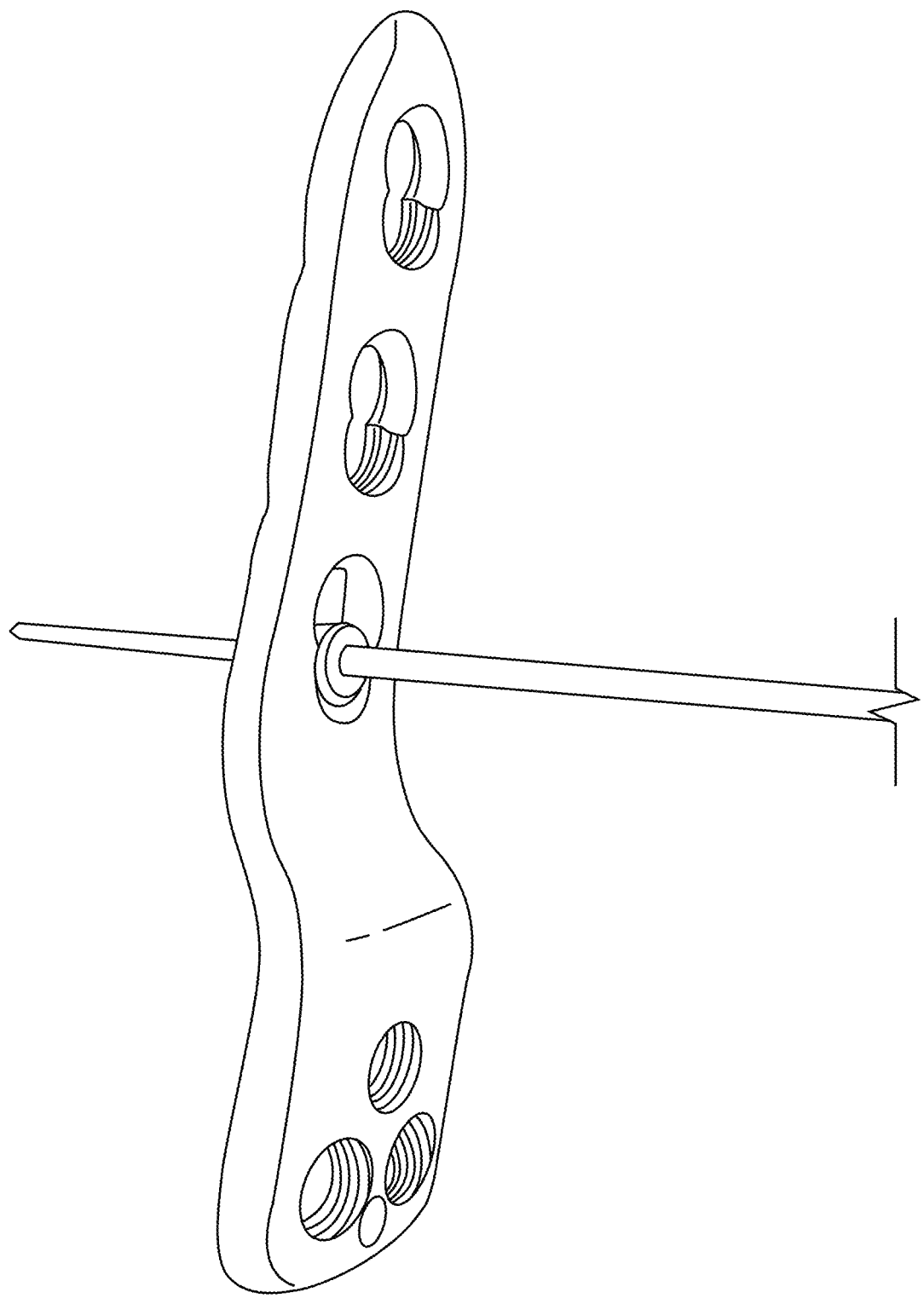
Figure 12A:
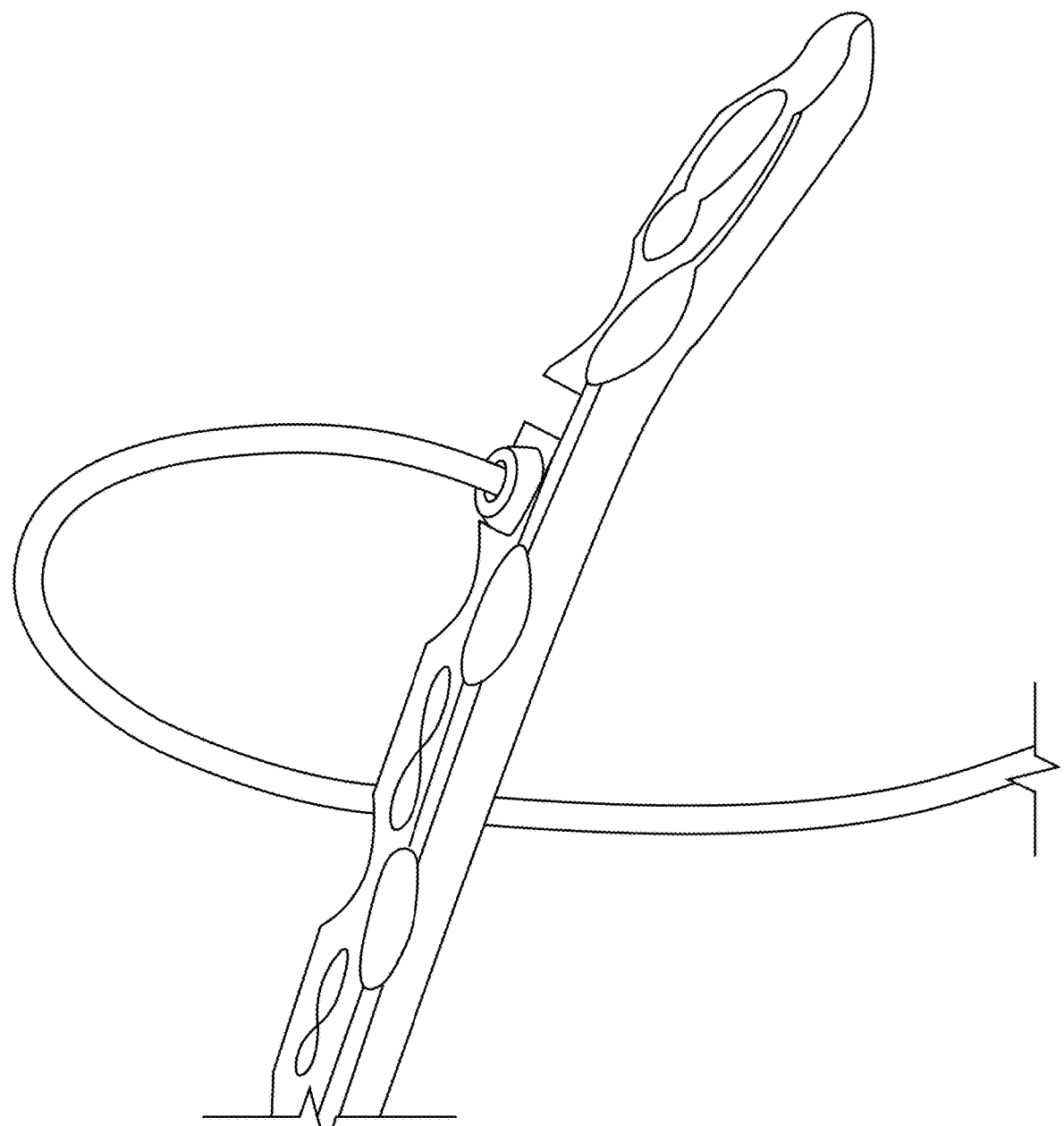
FIGS. 12A and 12B show perspective views of a Cerclage wire locked to the plate by the double-locking cannulated.
Figure 12B:
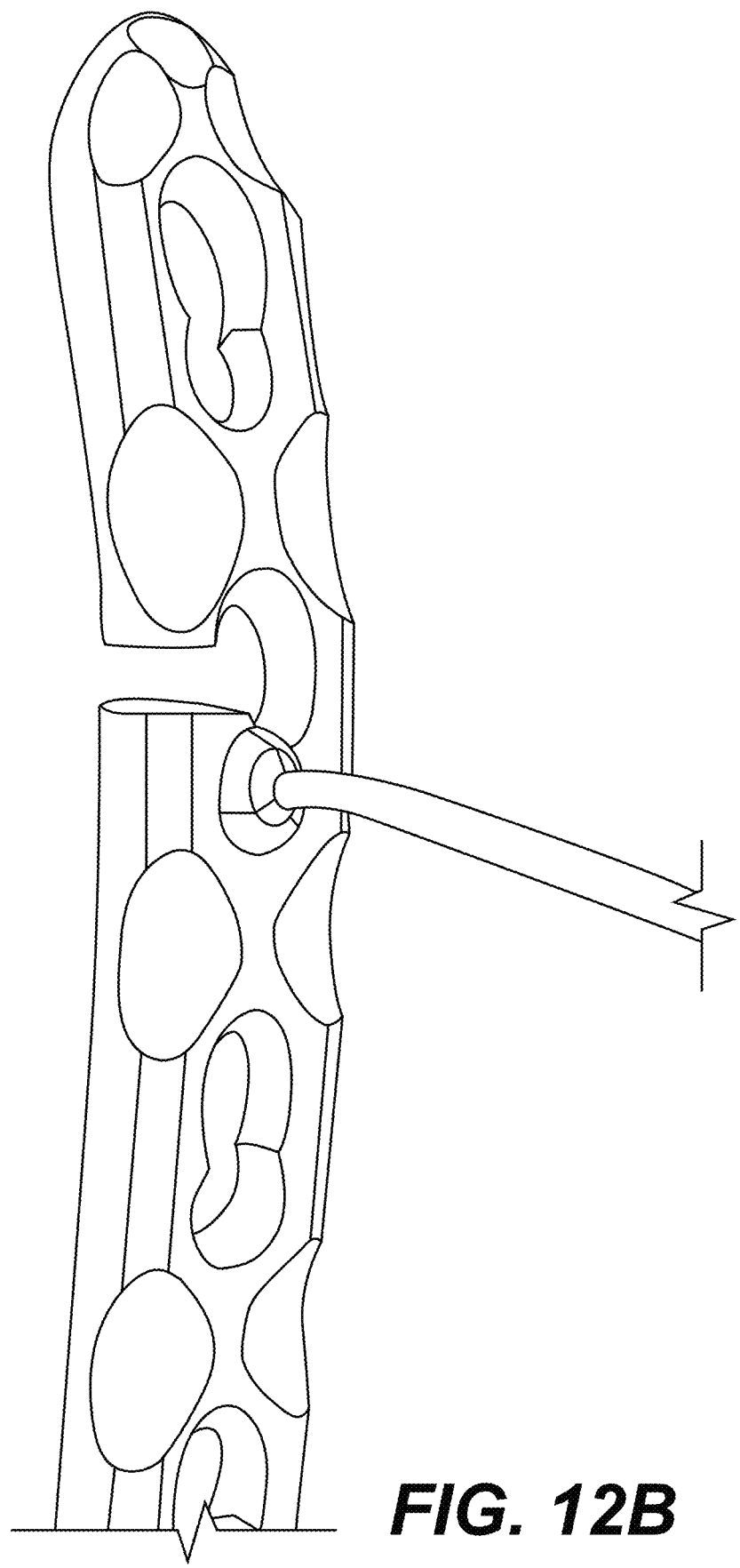
Figure 13A:
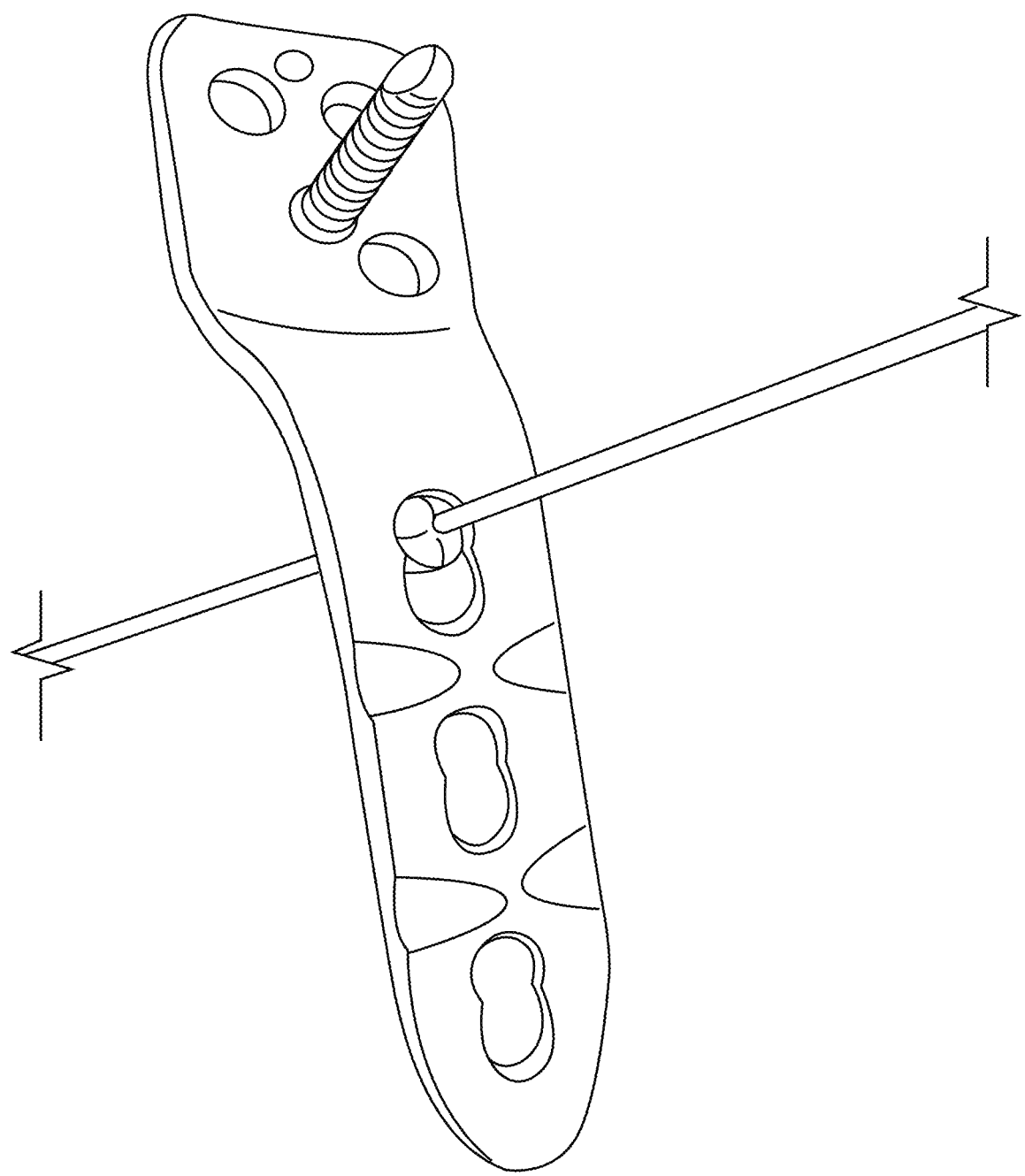
FIGS. 13A and 13B how a perspective view of a locked plate integrating locked screws and locked Kirschner hybrid bone anchoring systems and of a locked plate with association of locked and locked Kirschner screws showing the cannulated Kirschner locking screwdriver.
Figure 13B:
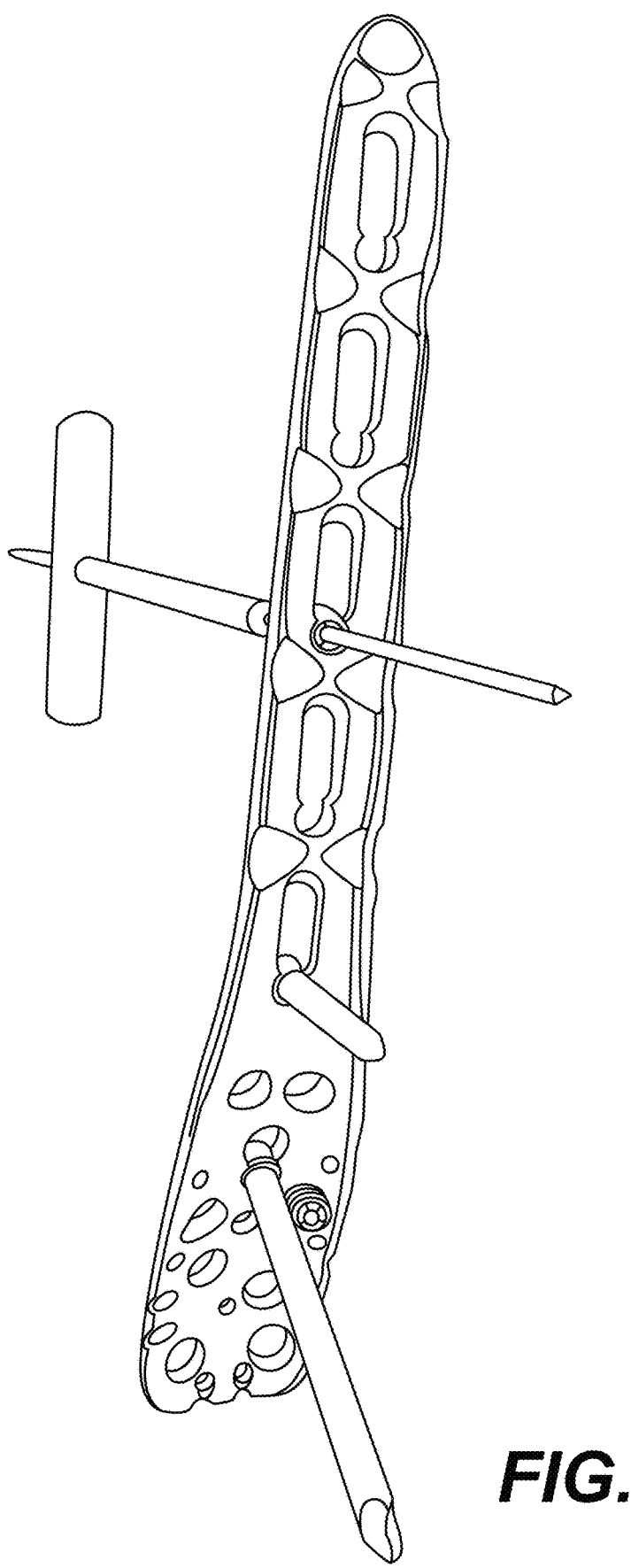

According to FIG. 8C, a lateral locked plate (a) is shown, with characteristics similar to the plate shown in FIG. 8B, which is also associated with an internal helical locked plate (b), with the same characteristics as described above, but in this case the bone transport is retrograde, by positioning the motor (c) in the distal sector of the lateral straight plate.

Having specifically described and determined the nature of the present invention and the manner in which it is to be implemented, the following is hereby claimed as proprietary and of exclusive right:

1. An internal extramedullary bone lengthening device with dynamic axial stabilization comprising:
   two bone fixation elements, comprising a first bone fixation element, configured as a locked plate-like system with bone fixation in a proximal sector and a distal sector, the first bone fixation element configured to allow use of a double-locking canulated assembly as a form of bone fixation which, in turn, allows for bone fixation by tension Kirschner wires and/or tension cerclage wires, the first bone fixation element having a bone anchoring element in a central sliding area, which is configured to move through a chamber guided by a central threaded rod that passes through the chamber, the central sliding area configured to support the Kirschner wires and/or the tension cerclage wires;
   a motor, disposed on a fixed part of the first bone fixation element, configured to rotate the central threaded rod, wherein the central sliding area comprises side wings that slide through an intermediate part of the first bone fixation element and prevent the central area from rotating while sliding down the central threaded rod.

\* \* \* \* \*